United States Patent [19]

Aungst et al.

[11] Patent Number: 4,757,062
[45] Date of Patent: Jul. 12, 1988

[54] SUBSTITUTED BENZOATE ESTER PRODRUGS OF ESTROGENS

[75] Inventors: Bruce J. Aungst; Munir A. Hussain, both of Wilmington, Del.

[73] Assignee: E. I. Du Pont de Nemours and Company, Wilmington, Del.

[21] Appl. No.: 793,892

[22] Filed: Nov. 1, 1985

[51] Int. Cl.$^4$ ............................ A61K 31/56; C07J 1/00
[52] U.S. Cl. ..................................... 514/182; 260/397.5
[58] Field of Search ....................... 260/397.5; 514/182

[56] References Cited

U.S. PATENT DOCUMENTS

| | | | |
|---|---|---|---|
| 2,054,271 | 9/1936 | Schwenk et al. | 260/103 |
| 2,243,887 | 6/1941 | Serini et al. | 260/397.5 |
| 2,251,939 | 8/1941 | Kathol | 260/397.5 |
| 2,265,976 | 12/1941 | Inhoffen et al. | 260/210 |
| 2,267,257 | 12/1941 | Ruzicka | 260/397.5 |
| 3,347,880 | 10/1967 | Robinson | 260/397.5 |
| 3,624,113 | 11/1971 | Ercoli et al. | 260/397.5 |
| 3,634,404 | 1/1972 | Marshall | 260/239.55 |
| 3,647,784 | 3/1972 | Stein et al. | 260/239.55 |
| 4,096,239 | 6/1978 | Katz et al. | 424/21 |
| 4,110,324 | 8/1978 | Gueritee | 260/239.5 |
| 4,191,697 | 3/1980 | Jouquey et al. | 260/397.5 |

FOREIGN PATENT DOCUMENTS

| | | |
|---|---|---|
| 0004898 | 5/1979 | European Pat. Off. . |
| 0030299 | 2/1981 | European Pat. Off. . |
| 2506548 | 8/1976 | Fed. Rep. of Germany . |
| 3144049 | 5/1983 | Fed. Rep. of Germany . |
| 83130 | 8/1971 | German Democratic Rep. . |
| 81034 | 1/1983 | Romania . |
| 1039447 | 8/1966 | United Kingdom . |

OTHER PUBLICATIONS

Chemical Abstracts vol. 42 (1964) #8097d; Fuchs et al.
Tsukuda, Y. et al., *J. Chem. Soc.*, (B), 1387 (1968).
Gardi, R., et al., *J. Med. Chem.*, 16, 123 (1973).
Doerfler, H. D., et al., *Stud. Biophys.*, 80, 59 (1980).
Elian, M., et al., *Eur. J. Med. Chem. Chim. Ther.*, 18, 385 (1983).
Brandau, W., et al., Chemical abstracts vol. 101 (1984) #126019k.
*The Textbook of Organic Medicinal and Pharmaceutical Compounds*, 5th Ed., P. 707.

*Primary Examiner*—Leonard Schenkman
*Assistant Examiner*—Joseph A. Lipovsky

[57] ABSTRACT

Substituted benzoate ester prodrugs of $\beta$-estradiol and ethynyl estradiol are provided which have improved bioavailability and extended duration of action when administered orally.

32 Claims, 1 Drawing Sheet

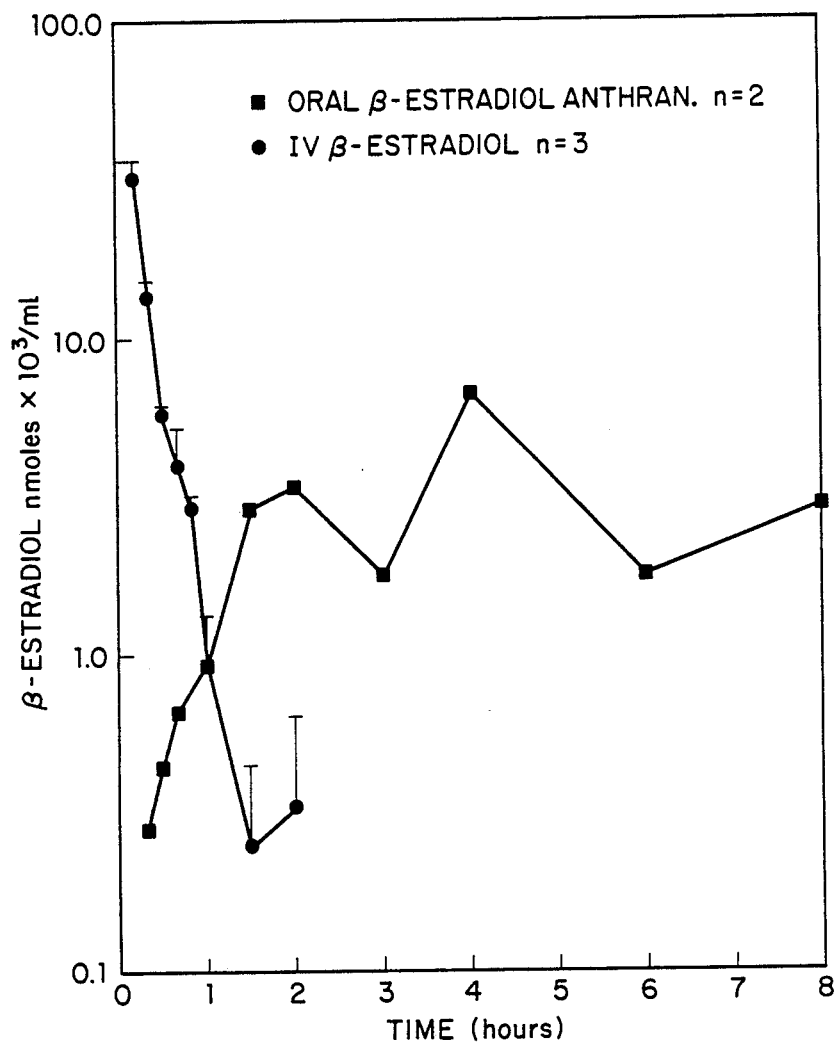

SUBSTITUTED BENZOATE ESTER PRODRUGS OF ESTROGENS

BACKGROUND OF THE INVENTION

1. Field of Invention

This invention relates to substituted benzoate ester prodrug derivatives of estrogens, pharmaceutical compositions containing prodrugs of estrogens, methods of contraception and treatments of disorders related to estrogen insufficiency using the prodrugs, and methods for preparing the prodrugs.

Prior Art

β-estradiol is the primary biosynthetic product found in mammalian estrogenic hormones, and is the most potent naturally occurring estrogen. Extensive literature exists on the biochemistry and physiology of this substance, and on its use in hormone replacement therapy and contraception. Although extremely potent when administered parenterally, this compound elicits greatly reduced estrogenic effects when administered orally.

Ethynyl estradiol is a semi-synthetic estrogen, first reported by Inhoffen et al., Chem. Ber., 71, 1024 (1938). This compound provides greater estrogenic activity than β-estradiol when administered orally, and is widely used in hormone replacement therapy and contraception. This compound and its preparation is disclosed in U.S. Pat. No. 2,243,887, issued June 3, 1941, to A. Serini et al.; U.S. Pat. No. 2,251,939, issued Aug. 12, 1941, to J. Kathol; U.S. Pat. No. 2,265,976, issued Dec. 9, 1941, to H. H. Inhoffen et al.; and U.S. Pat. No. 2,267,257, issued Dec. 23, 1941, to L. Ruzicka.

β-estradiol 3-benzoate is disclosed by U.S. Pat. No. 2,054,271 (to Schwenk and Hildebrandt, 1936), and is widely used as a long-acting parenteral estrogenic drug for intramuscular injection.

Of the simple esters of β-estrodiol such as the benzoate, the acetate and the propionate, which all result in prolonged activity when administered intramuscularly; the benzoate is most preferred because it is absorbed more slowly. These compounds show a marked decrease in activity when administered orally due to destruction by the intestinal bacteria and the liver.

Many disclosures of synthetic substances structurally related to estradiol which have been esterified with benzoic acid or hetero-aryl carboxylic acids can be found in the literature, with estrogenic and non-estrogenic pharmacological activities reported. A few examples are U.S. Pat. No. 3,347,880 (to Robinson, 1967), U.S. Pat. No. 3,634,404 (to Marshall, 1972), U.S. Pat. No. 4,110,324 (to Guéritée, 1978), Eur. Patent Appl. 4898 (to Prezewowsky et al., 1979), and German Pat. No. 3,144,049 (to Bermejo-Gonzales et al., 1983).

β-Estradiol 3-p-bromobenzoate was reported by Y. Tsukuda et al., J. Chem. Soc., (B), 1387 (1968), and was used in an X-ray crystal structure determination.

Substituted benzoate esters of β-estradiol with the formula

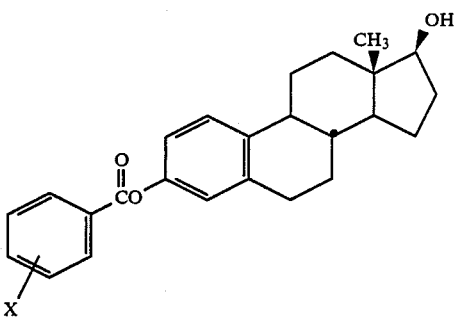

wherein X=4-CH$_3$, 4-F, 2-Cl, 3-Cl, 4-Cl, 4-NO$_2$, 4-OCH$_3$, or 4-OC$_5$H$_9$ are disclosed in German Patent No. 1,961,984 (1970, to Ercoli et al) and in Gardi et al., J. Med. Chem., 16, 123 (1973) as intermediates to orally active 17-enolethers of these compounds.

4-Alkoxybenzoate esters of β-estradiol are reported by Doerfler et al., Stud. Biophys., 80, 59 (1980). The phase transition energetics of these compounds as liquid crystals are described in this publication.

Substituted aminomethylbenzoate esters of β-estradiol with the formula

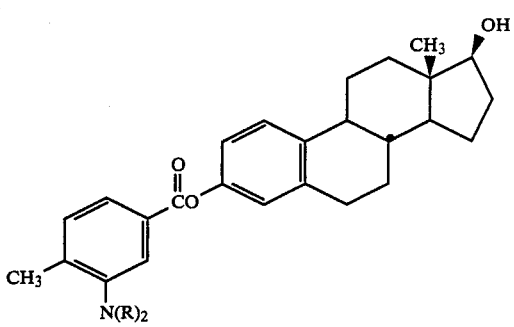

wherein R=CH$_2$CH$_2$Cl or —CH(CH$_3$)CH$_2$Cl are disclosed by M. Elian et al., Eur. J. Med. Chem. Chim. Ther., 18, 385 (1983), and by Romanian Patent No. 81,034 (1983, to Duvaz et al.). These compounds are described as alkylating agents with antineoplastic activities.

The radio-labelled 2-iodobenzoate of estradiol is reported by Brandau et al., Nuklearmedizin, Suppl., 20, 726 (1984), and was prepared by iodine-131 exchange with the corresponding 2-bromobenzoate ester.

The oral administration of many drugs will elicit a substantially lesser response as compared to an equal dose administered parenterally. This reduction in potency commonly results from the extensive metabolism of the drug during its transit from the gastrointestinal tract to the general circulation. For example, the liver and intestinal mucosa, through which an orally administered drug passes before it enters the systemic circulation, are very active enzymatically and can thus metabolize the drug in many ways.

When an orally administered drug is rapidly metabolized to an inactive or significantly less active form by the gastrointestinal system or liver prior to entering the general circulation, its bioavailability is low. In certain circumstances, this problem can be circumvented by administering the drug by another route. Examples of such alternative routes include nasal (propranolol), sublingual (nitroglycerin) and inhalation (cromolyn sodium). Drugs administered by these routes avoid hepatic and gut-wall metabolism on their way to the systemic circulation.

In some instances, the presystemic metabolism of certain orally administered drugs can be overcome by derivatization of the functional group in the molecule that is susceptible to gastrointestinal or hepatic metabolism. This modification protects the group from metabolic attack during the absorption process or first pass through the liver. However, the masking group must ultimately be removed to enable the drug to exert its maximum effect. This conversion may take place in blood or tissue. (Since the chemical group used to alter the parent drug will eventually be released into the body, it must be relatively non-toxic.) These types of masked drugs are usually referred to as prodrugs.

There are a number of examples in the literature which demonstrate the feasibility of the prodrug concept. However, it is apparent from these published studies that each drug class must be considered by itself. There is no way to accurately predict which prodrug structure will be suitable for a particular drug. A derivative which may work well for one drug may not do so for another. Differences in the absorption, metabolism, distribution, and excretion among drugs do not permit generalizations to be made about prodrug design.

β-estradiol, although a potent estrogenic compound, undergoes extensive gastrointestinal and/or hepatic first-pass metabolism upon oral delivery, and thus has very significantly reduced bioavailability. Ethynyl estradiol is a potent semi-synthetic estrogen which shows enhanced oral bioavailability over β-estradiol, but still suffers from gastrointestinal and/or hepatic first pass metabolism after oral dosing.

None of the references cited, nor any known reference, suggest the novel substituted benzoate esters of estrogens of the present invention, or their desirability as prodrugs of estrogens. Particularly unexpected is the fact that the substituted benzoate esters of this invention exhibit significantly improved bioavailability and extended duration of action when administered orally.

SUMMARY OF THE INVENTION

According to the present invention there is provided a compound of the formula:

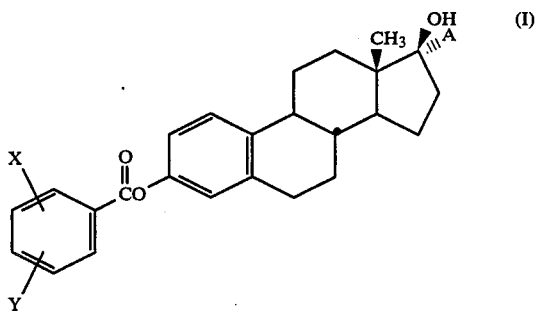

wherein
A is H or C≡CH;
X and Y individually are selected from H, NHR$^1$, NR$^1$R$^2$, and OR$^2$;
R$^1$ is H, alkyl of 1–4 carbon atoms, or COR$^3$;
R$^2$ is alkyl of 1–4 carbon atoms, or COR$^3$; and
R$^3$ is H or alkyl of 1–4 carbon atoms;

with the proviso that if X is H, then Y is not H or 4-OR$^2$ or a pharmaceutically suitable salt thereof.

Also provided is a pharmaceutical composition consisting essentially of a compound of the formula:

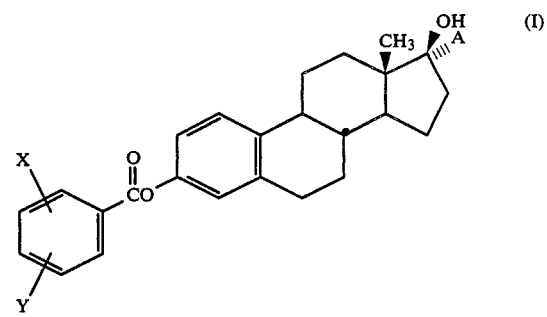

wherein
A is H or C≡CH;
X and Y individually are H, NHR$^1$, NR$^1$R$^2$, or OR$^2$;
R$^1$ is H, alkyl of 1–4 carbon atoms, or COR$^3$;
R$^2$ is alkyl of 1–4 carbon atoms, or COR$^3$;
R$^3$ is H or alkyl of 1–4 carbon atoms; with the proviso that one of X or Y is other than H
or a pharmaceutically suitable salt thereof.

Especially preferred is a pharmaceutical composition formulated for oral administration.

Further provided is a method of preventing or inhibiting conception, or treating disorders which respond to estrogen therapy, in a mammal comprising: administering to the mammal an effective estrogenic amount of at least one of the immediately aforesaid compounds. It is especially preferred to administer the compounds orally.

Additionally provided is a process for preparing a compound of the invention comprising: contacting β-estradiol or ethynyl estradiol, optionally in the presence of a base, with an acylating agent selected from the group consisting of

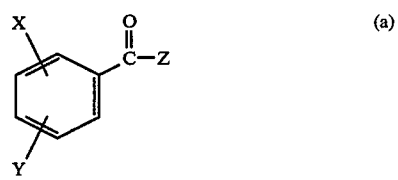

wherein
Z is Cl,

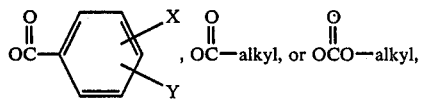

and X and Y are as defined above;
and

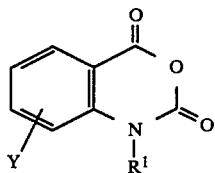

(b)

wherein R¹ and Y are as defined above.

BRIEF DESCRIPTION OF THE DRAWING

The drawing is a graph showing β-estradiol plasma concentration of tritiated β-estradiol after intravenous administration of β-estradiol and oral administration of tritiated β-estradiol 3-anthranilate.

DETAILED DESCRIPTION OF THE INVENTION

Preferred compounds are those of Formula (I) wherein:
X is $NHR^1$ or $OR^2$; where
$R^1$ is H or alkyl of 1–4 carbon atoms;
$R^2$ is $COR^3$;
$R^3$ is alkyl of 1–4 carbon atoms; and Y is H.
More preferred are compounds of Formula (I) wherein:
X is $NH_2$ or $OC(O)CH_3$; and Y is H.
Specifically preferred are:
β-estradiol 3-anthranilate (A=H, X=2-$NH_2$, Y=H)
Ethynyl estradiol 3-anthranilate hydrochloride (A=−C≡CH, X=2-$NH_2$, Y=H)
β-estradiol 3-(O-acetyl salicylate) (A=H, X=2-$OC(O)CH_3$, Y=H).

Synthesis

The compounds of the present invention can be prepared by contacting β-estradiol or ethynyl estradiol with an acylating agent, optionally in the presence of a catalyst. The acylating agents and catalysts used as starting reactants to make the compounds of Formula (I) are well known and available commercially.

The acylating agents used in the process to prepare the prodrugs of Formula (I) include substituted benzoyl halides, substituted benzoic anhydrides, mixed anhydrides, and isatoic anhydrides.

As used herein, the term "Method A" refers to the process for preparing a compound of Formula (I) wherein the acylating agent is a substituted benzoyl halide, a substituted benzoic anhydride, or a mixed anhydride.

As used herein, the term "Method B" refers to the process for preparing a compound of Formula (I) wherein the acylating agent is an isatoic anhydride.

METHOD A

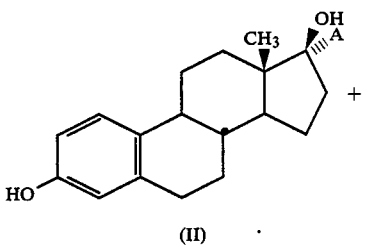

(II)

-continued
METHOD A

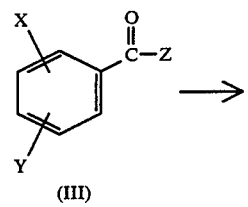

(III)

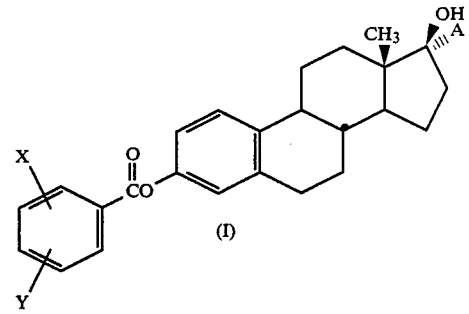

(I)

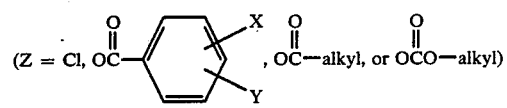

(Z = Cl, OC—, OC—alkyl, or OCO—alkyl)

Method A provides compounds of Formula (I) wherein X and Y individually are selected from H, $OR^2$, or $NR^1R^2$, wherein $R^1$ and $R^2$ individually are $C_1$–$C_4$ alkyl or $COR^3$, provided that at least one of X or Y is $OR^2$ or $NR^1R^2$.

In method A, the estrogenic compound (II) is allowed to react with an activated acylating agent (III), such as a substituted benzoyl chloride, benzoic anhydride or mixed anhydride, wherein X and Y are not OH or $NHR^1$, in an aprotic solvent such as methylene chloride, tetrahydrofuran, or 1,2-dimethoxyethane, preferably in the presence of an organic base catalyst such as triethylamine, N-methylmorpholine or pyridine, or an inorganic base such as sodium carbonate. A solution of the activated benzoate derivative in the reaction solvent is added to a solution of the estrogenic compound in the reaction solvent containing the base at a temperature ranging from 0° C. to the boiling point of the solvent, generally from 0° C. to room temperature being preferred. The reactants are kept in contact from 0.5 to 24 hours, generally 2 to 20 hours.

The process of Method A is illustrated by Example 1.

METHOD B

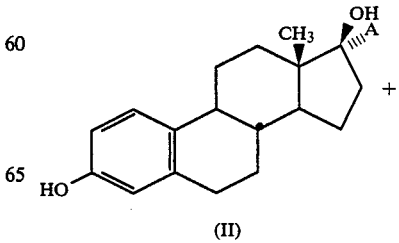

(II)

-continued
METHOD B

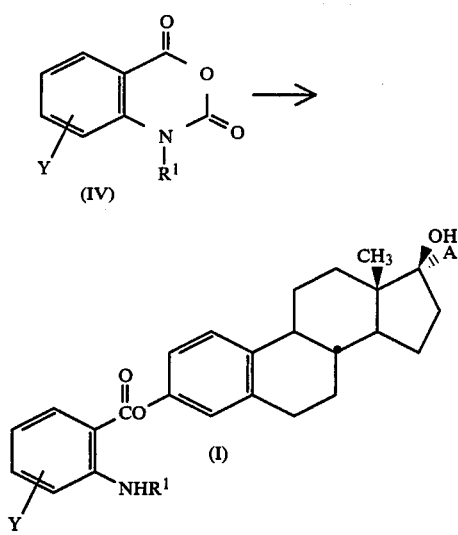

Method B provides compounds of Formula (I) wherein X is 2-NHR¹.

In method B, the estrogenic compound (II) is dissolved in a dipolar aprotic solvent, such as N,N-dimethylformamide (DMF), dimethylsulfoxide (DMSO), N-methylpyrrolidinone, N,N-dimethylacetamide (DMAC), or tripyrrolidinophosphine oxide. An isatoic anhydride (IV) is added, followed by a base catalyst, such as 4-dimethylaminopyridine, 4-pyrrolidinopyridine, or 4-piperidinopyridine. The solution is heated at 50° C. to 150° C. for one to five hours under nitrogen.

In method B, compounds with various groups represented by R¹ are prepared from the corresponding substituted isatoic anhydrides, (IV).

The process of Method B is illustrated by Examples 2 and 3.

EXAMPLE 1

β-Estradiol 3-O-acetylsalicylate

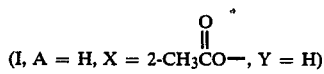

(I, A = H, X = 2-CH₃CO—, Y = H)

To a solution of triethylamine (8 mL, 0.055 mole) in dichloromethane (120 mL) at room temperature was added β-estradiol (2.72 g, 0.01 mole). The mixture was stirred until a clear solution resulted, and then was cooled to between 0° C. and 5° C. A solution of acetylsalicyloyl chloride (2.2 g, 0.011 mole) was added dropwise with stirring. After addition was complete, the ice bath was removed and the mixture was stirred at ambient temperature for 5 hours. It was then washed with 10% aqueous sodium carbonate, then with water, and was dried over sodium sulfate, filtered and evaporated. The residue was triturated with ether, filtered and air-dried to provide the title compound (69% yield) as a solid, mp 185°–188° C.

NMR spectrum (DMSO-D₆): δ 0.7 (s, 3H, methyl), 1.06–3.63 (m, 16H, aliphatic), 2.25 (s, 3H, acetyl methyl), 4.58 (d, 1H, hydroxy), 6.9–8.16 (m, 7H, aromatic).

Mass spectrum: m/z 435.

Elemental analysis: calculated for $C_{27}H_{30}O_5$: C, 74.63%; H, 6.96%. Found: C, 74.49%; H, 7.02%.

EXAMPLE 2

β-Estradiol 3-anthranilate (I, A=H, X=2-NH₂, Y=H

A mixture of β-estradiol (0.27 g, 1 mmole), isatoic anhydride (0.18 g, 1.1 mmole) and 4-dimethylaminopyridine (0.13 g, 1.1 mmole) in N,N-dimethylformamide (5 mL) was heated at 80° C. for 4 hours. After cooling, 20 mL of 10% aqueous sodium chloride solution was added, and the mixture was stirred for 0.5 hours. The precipitate was collected by filtration, washed with water and air-dried. The resulting solid was dissolved in ethyl acetate and precipitated by adding hexane. After filtration and drying, the title compound (65% yield) was obtained as a solid, mp 203°–205° C.

NMR spectrum (DMSO-D₆): δ 0.7 (s, 3H, methyl), 1.13–2.93 (m, 16H, aliphatic), 4.53 (d, 1H, hydroxy), 6.53–7.9 (m, 7H, aromatic), 6.72 (s, 2H, amine).

Mass spectrum: m/z 392, 272.

Elemental analysis: Calculated for $C_{25}H_{29}NO_3$: C, 76.6%; H, 7.46%; N, 3.58%. Found: C, 76.57%; H, 7.49%; N, 3.55%.

EXAMPLE 3

Ethynyl estradiol 3-anthranilate hydrochloride (I, A=C≡CH, X=2-NH₂, Y=H)

Using the procedure of Example 2, ethynyl estradiol was treated with isatoic anhydride to provide ethynyl estradiol 3-anthranilate. The crude product was dissolved in a mixture of ether and methylene chloride and treated with gaseous hydrogen chloride. The precipitate was collected by filtration, washed with ether and air-dried to provide the title compound (65% yield) as a solid, mp 196°–198° C.

NMR spectrum of the free base (DMSO-D₆): δ 0.83 (s, 3H, methyl), 1.32–2.9 (m, 16H, aliphatic), 5.4 (s, 1H, hydroxy), 6.57–7.93 (m, 7H, aromatic), 6.75 (s, 2H, amine).

Mass spectrum: m/z 415.

Elemental analysis: Calculated for $C_{27}H_{30}NO_3Cl$: C, 71.75%; H, 6.69%; N, 3.10%. Found: C, 71.50%; H, 6.76%; N, 3.04%.

The compounds of Examples 1 to 3 and several other compounds which can be prepared by the same procedures are summarized in the table below.

TABLE

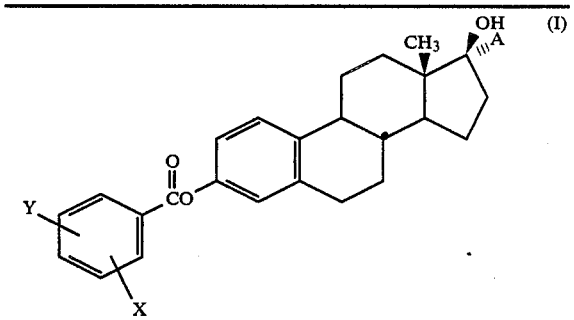

| Example | A | X | Y | yield | mp |
|---|---|---|---|---|---|
| 1 | H | 2-CH₃CO₂ | H | 69% | 185–188° C. |
| 2 | H | 2-NH₂ | H | 65% | 203–205° C. |

TABLE-continued

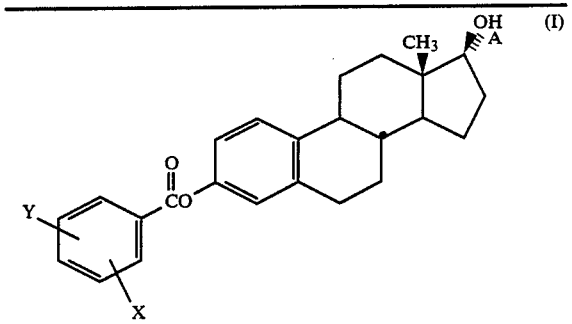

| Example | A | X | Y | yield | mp |
|---|---|---|---|---|---|
| 3 | C≡CH | 2-NH$_2$.HCl | H | 65% | 196–198° C. |
| 4 | C≡CH | 2-CH$_3$CO$_2$ | H | | |
| 5 | H | 2-CH$_3$CO$_2$ | H | | |
| 6 | H | 3-CH$_3$O | 5-CH$_3$O | | |
| 7 | C≡CH | 2-CH$_3$O | 4-CH$_3$O | | |
| 8 | H | 3-CH$_3$O | 4-CH$_3$O | | |
| 9 | H | 3-NH$_2$ | H | | |
| 10 | C≡CH | 3-NH$_2$.HCl | H | | |
| 11 | H | 2-CH$_3$NH | H | | |
| 12 | C≡CH | 2-CH$_3$NH | H | | |
| 13 | H | 4-CH$_3$CONH | H | | |
| 14 | H | 2-(CH$_3$)$_2$N | H | | |

DOSAGE FORMS

The prodrugs of Formula (I) can be administered to treat disorders which respond to estrogen therapy or prevent conception by any means that produces contact of the active agent with the agent's site of action in the body of a mammal. They can be administered by any conventional means available for use in conjunction with pharmaceuticals, either as individual agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of prodrug can be up to 7 milligrams daily. Ordinarily, when the more potent compounds of this invention are used, up to 2 milligrams, given once daily or in sustained release form, is effective to obtain desired results.

Dosage forms (compositions) suitable for internal administration contain from about 0.5 to 7 (preferably about 0.5 to 2) milligrams of prodrug per unit. In these pharmaceutical compositions the prodrug of Formula (I) will ordinarily be present in an amount of about 0.5 to 95% by weight based on the total weight of the composition.

The prodrug is preferably administered orally in solid dosage forms, such as capsules, tablets, and powders, or in liquid dosage forms, such as elixirs, syrups, and suspensions.

Gelatin capsules contain the prodrug of Formula (I) and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

Suitable pharmaceutical carriers are described in *Remington's Pharmaceutical Sciences*. A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 1 milligram of powdered prodrug of Formula (I), 150 milligrams of lactose, and 2 milligrams of magnesium stearate.

Soft Gelatin Capsules

A suspension of a prodrug of Formula (I) in a digestable oil such as soybean oil, cottonseed oil or olive oil is prepared and injected by means of a positive displacement pump into gelatin to form soft gelatin capsules containing 1 milligram of the prodrug. The capsules are washed in petroleum ether and dried.

Tablets

A large number of tablets are prepared by conventional procedures so that the dosage unit is 1 milligram of the prodrug of Formula (I), 0.2 milligrams of colloidal silicon dioxide, 5 milligrams of magnesium stearate, 62.8 milligrams of microcrystalline cellulose, 11 milligrams of starch and 120 milligrams of lactose. Appropriate coatings may be applied to increase palatability or delay absorption.

Suspension

An aqueous suspension is prepared for oral administration so that each 5 milliliters contain 1 milligram of finely divided prodrug, 200 milligrams of sodium carboxymethyl cellulose, 5 milligrams of sodium benzoate, 1.0 grams of sorbitol solution, U.S.P., and 0.025 milliliters of vanillin.

Utility

Test results indicate that the prodrugs useful in the present invention provide greatly enhanced bioavailability of estrogens from orally administered dosages. Additionally, greatly enhanced duration of action results after oral dosing with these prodrugs the present invention.

Method

Dogs were administered the drug intravenously and orally, and the prodrugs were administered orally. Usually, doses were administered as solutions in PEG400-/water (3:1). Plasma was collected and frozen until analysis of drug concentration was performed. The area under the plasma drug concentration versus time curve (AUC) was calculated for each animal. Bioavailability (F) was estimated by:

$$F = \frac{AUC(po) \times \text{Dose}(iv)}{AUC(iv) \times \text{Dose}(po)} \times 100$$

F represents the percentage of the administered dose absorbed into plasma.

RESULTS FOR β-ESTRADIOL 3-ANTHRANILATE

When β-estradiol was administered orally, none of this drug could be detected in the plasma. After intravenous administration (0.125μ mole/kg), β-estradiol was detected in the plasma and displayed an average elimination half-life of 11.8 minutes. No β-estradiol could be detected at 3 hours after the intravenous dose was administered.

When β-estradiol 3-anthranilate of Example 2 was administered orally at a dose of 0.25μ mole/kg, β-estradiol was detected in the plasma at concentrations of about 0.0025 nmole/mL. The estimated oral bioavailability of β-estradiol from the administered 3-anthranilate ester averaged 74.5% (two dogs). The plasma concentrations remained at about 0.0025 nmole/mL at 8 hours after the oral dose was administered.

A graph of β-estradiol plasma concentration vs. time for one experiment is shown in the drawing.

β-estradiol 3-anthranilate, when administered orally, thus provides much higher bioavailability of β-estradiol (74.5%) than a corresponding oral dose of β-estradiol itself (in which β-estradiol was not detectable in plasma under the analytical conditions used). Also, orally administered β-estradiol 3-anthranilate provides an appreciable plasma concentration of β-estradiol for a much longer period of time than an intravenous dose of β-estradiol (greater than 8 hours, compared to less than 3 hours).

What is claimed is:

1. A compound of the formula:

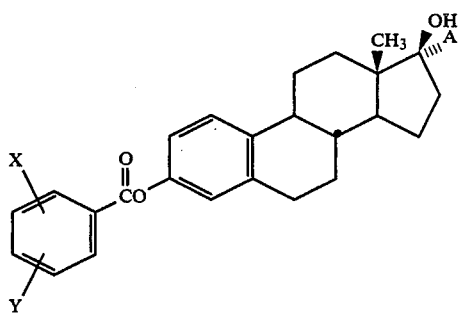

wherein
A is H or C≡CH;
Y is H;
X is NR$^1$R$^3$ or OR$^2$;
R$^1$ is H, alkyl of 1–4 carbon atoms, or COR$^3$;
R$^2$ is COR$^3$; and
R$^3$ is H or alkyl of 1–4 carbon atoms;
or a pharmaceutically suitable salt thereof.

2. A compound of claim 1 wherein A is H.

3. A compound of claim 1 wherein X is NHR$^1$ or OR$^2$ wherein R$^1$ is H or alkyl of 1–4 carbon atoms, R$^2$ is COR$^3$ where R$^3$ is alkyl of 1–4 carbon atoms.

4. A compound of claim 3 wherein A is H.

5. A compound of claim 4 wherein X is NH$_2$ or OC(O)CH$_3$.

6. The compound of claim 5 which is β-estradiol 3-anthranilate.

7. The compound of claim 5 which is β-estradiol 3-(O-acetyl salicylate).

8. A compound of claim 3 wherein A is C≡CH.

9. A compound of claim 8 wherein X is NH$_2$.

10. The compound of claim 9 which is ethynyl estradiol 3-anthranilate hydrochloride.

11. A pharmaceutical composition consisting essentially of a pharmaceutical carrier and an effective estrogenic amount of a compound of claim 1.

12. A composition of claim 11 which is in oral dosage form.

13. A composition of claim 12 wherein A is H.

14. A composition of claim 12 wherein X is NHR$^1$ or OR$^2$ wherein R$^1$ is H or alkyl of 1–4 carbon atoms, R$^2$ is COR$^3$ where R$^3$ is alkyl of 1–4 carbon atoms.

15. A composition of claim 14 wherein A is H.

16. A composition of claim 14 wherein A is C≡CH.

17. A composition of claim 15 wherein X is NH$_2$ or OC(O)CH$_3$.

18. A composition of claim 16 wherein X is NH$_2$.

19. A composition of claim 12 wherein the estrogenic compound is β-Estradiol 3-Anthranilate.

20. A composition of claim 12 wherein the estrogenic compound is β-estradiol 3-(O-acetyl salicylate).

21. A composition of claim 12 wherein the estrogenic compound is ethynyl estradiol 3-Anthranilate hydrochloride.

22. A method of preventing or inhibiting conception, or treating disorders which respond to estrogen therapy, in a mammal comprising: administering to the mammal an effective estrogenic amount of a compound of claim 1.

23. A method of claim 22 wherein the compound is administered orally.

24. A method of claim 23 wherein A is H.

25. A method claim 23 wherein X is NHR$^1$ or OR$^2$ wherein R$^1$ is H or alkyl or 1–4 carbon atoms, R$^2$ is COR$^2$ where R$^3$ is alkyl of 1–4 carbon atoms.

26. A method of claim 25 wherein A is H.

27. A method of claim 25 wherein A is C≡CH.

28. A method of claim 26 wherein X is NH$_2$ or OC(O)CH$_3$.

29. A method of claim 27 wherein X is NH$_2$.

30. A method of claim 23 wherein the estrogenic compound is β-estradiol 3-Anthranilate.

31. A method of claim 23 wherein the estrogenic compound is β-estradiol 3-(O-acetyl salicylate).

32. A method of claim 23 wherein the estrogenic compound is ethynyl estradiol 3-anthranilate hydrochloride.

* * * * *